United States Patent [19]
Commereuc et al.

[11] Patent Number: 6,031,145
[45] Date of Patent: Feb. 29, 2000

[54] CATALYTIC COMPOSITION AND PROCESS FOR OLIGOMERISING ETHYLENE IN PARTICULAR TO 1-BUTENE AND/OR 1-HEXENE

[75] Inventors: Dominique Commereuc, Meudon; Sébastien Drochon, Rueil Malmaison; Lucien Saussine, Croissy sur Seine, all of France

[73] Assignee: Institut Francais du Petrole, Rueil-Malmaison Cedex, France

[21] Appl. No.: 09/098,647

[22] Filed: Jun. 17, 1998

[30] Foreign Application Priority Data

Jun. 17, 1997 [FR] France .................... 97 07613

[51] Int. Cl.[7] .............. C07C 2/24; B01D 31/00
[52] U.S. Cl. ............ 585/512; 502/150; 502/152; 502/153; 502/154; 502/169; 502/171; 585/500; 585/502; 585/510; 585/511; 585/520; 585/530; 585/532
[58] Field of Search ............... 502/150, 152, 502/153, 154, 169, 171; 585/500, 502, 510, 511, 512, 520, 530, 532

[56] References Cited

U.S. PATENT DOCUMENTS 4,016,343   4/1977   Hoff et al. .................. 526/106
5,856,257   1/1999   Freeman et al. ............. 502/152

FOREIGN PATENT DOCUMENTS

| 0 706 983 A1 | 4/1996 | European Pat. Off. . |
| 0 769 323 A1 | 4/1997 | European Pat. Off. . |
| 1 453 328 | 4/1966 | France . |
| 197 07 888 A1 | 9/1996 | Germany . |

*Primary Examiner*—Elizabeth D. Wood
*Attorney, Agent, or Firm*—Millen, White, Zelano & Branigan, P.C.

[57] ABSTRACT

A catalyst composition for a process of oligomerising ethylene to produce 1-butene and/or 1-hexene wherein the catalytic composition is obtained by mixing at least one chromium compound with at least one aryloxy aluminum compound with general formula $R_nAl(R'O)_{3-n}$ where R is a linear or branched hydrocarbyl radical containing 1 to 30 carbon atoms, R'O is an aryloxy radical containing 6 to 80 carbon atoms and n is a whole number which can take the values 0, 1 or 2, and with at least one other hydrocarbyl aluminum compound selected from tris(hydrocarbyl) aluminum compounds or chlorinated or brominated hydrocarbyl aluminum compounds.

27 Claims, No Drawings

CATALYTIC COMPOSITION AND PROCESS FOR OLIGOMERISING ETHYLENE IN PARTICULAR TO 1-BUTENE AND/OR 1-HEXENE

FIELD OF THE INVENTION

The present invention relates to a process for digomerizing ethylene, in particular to 1-butene and/or 1-hexene, and to the catalytic composition used.

BACKGROUND OF THE INVENTION

Processes for producing alpha olefins from ethylene generally lead to an ensemble of oligomers containing 4 to 30 carbon atoms, or even more than 30, and the olefins are then separated by distillation. Over the past few years, demand for lower oligomers, essentially 1-butene, 1-hexene and 1-octene, which are used as co-monomers with ethylene for the manufacture of linear low density polyethylene, has been increasing.

Few catalysts exist which selectively produce a particular oligomer, as is the case when dimerizing ethylene to 1-butene with a titanium based catalyst. However, chromium based catalysts are known to lead to the formation of mainly 1-hexene, with polyethylene to a greater or lesser extent, the proportion of butenes and octenes in the products being very small (R. M. Manyik, W. E. Walker, T. P. Wilson, J. Catal., 1977, 47, 197 and J. R. Briggs, J. Chem. Soc., Chem. Commun. 1989, 674 and references cited therein). Catalysts which enable selective trimerization of ethylene have recently been claimed (U.S. Pat. No. 5,198,563, U.S. Pat. No. 5,288,823, U.S. Pat. No. 5,382,738, European patent EP-A-0 608 447, EP-A-0 611 743, EP-A-0 614 865). Such catalysts are prepared from a chromium salt and a metal amide, in particular a pyrrolide. Other catalysts use an aluminoxane and a chromium complex with a chelating phosphine (U.S. Pat. No. 5,550,305).

SUMMARY OF THE INVENTION

We have now discovered in the present invention that a catalytic composition obtained by mixing at least one chromium compound with at least one aryloxy aluminum compound and with at least one hydrocarbyl aluminum compound has particular selectivity for the formation of 1-butene and/or 1-hexene by oligomerization of ethylene.

More precisely, the improved catalytic composition is obtained by mixing:
- at least one chromium compound which may contain one or more identical or different anions, for example selected from the group formed by halides, carboxylates, acetylacetonates, alkoxy anions and aryloxy anions;
- with at least one aryloxy aluminum compound with general formula $R_nAl(R'O)_{3-n}$ in which n is a whole number which can take the values 0, 1 or 2, R is a linear or branched hydrocarbyl radical containing 1 to 30 carbon atoms, and R'O is an aryloxy radical containing 6 to 80 carbon atoms;
- and with at least one hydrocarbyl aluminum compound with general formula $AlR''_mX_{3-m}$ where R'' is a hydrocarbyl radical containing 1 to 6 carbon atoms, X is a chlorine or bromine atom and m is a number from 1 to 3.

The chromium compound can be a chromium (II) or chromium (III) salt but also a salt with a different oxidation number which may contain one or more identical or different anions such as halides, carboxylates, acetylacetonates, alkoxy anions, or aryloxy anions. The chromium compounds preferably used in the invention are chromium (III) compounds as they are more accessible, but a chromium (I) or chromium (II) compound would also be suitable.

The chromium compounds selected can advantageously be dissolved in a hydrocarbon medium by complexing with an organic oxygen-containing compound such as an ether or an ester or a compound selected from the group formed by acetals and ketals, resulting from condensation of an aldehyde or a ketone with a mono-alcohol or a poly-alcohol, such as di-2,2-(2-ethylhexyloxy)propane.

The aryloxy aluminum compound is selected from aryloxy aluminum compounds with general formula $R_nAl(R'O)_{3-n}$ in which n is a whole number which can take the values 0, 1 or 2, R is a linear or branched hydrocarbyl radical containing 1 to 30 carbon atoms, for example alkyl, cycloalkyl, alkenyl, aryl, or substituted aralkyl, aryl or cycloalkyl, preferably a hydrocarbyl residue containing 2 to 10 carbon atoms. Non limiting examples of R are an ethyl, n-propyl, isopropyl, n-butyl, isobutyl, cyclohexyl, benzyl, diphenylmethyl, phenyl, 2-methylphenyl, or a 2,6-diphenylphenyl residue. R'O is an aryloxy radical containing 6 to 80 carbon atoms.

Preferred aryloxy aluminum compounds comprise an aryloxy radical R'O with general formula:

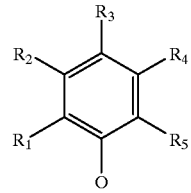

where $R_1$, $R_2$, $R_3$, $R_4$, $R_5$, which may be identical or different, represent a hydrogen, halogen or hydrocarbyl radical, for example alkyl, cycloalkyl, alkenyl, aryl, or substituted aralkyl, aryl or cycloalkyl, preferably containing 1 to 16 carbon atoms, in particular 1 to 10 carbon atoms. Non limiting examples of $R_1$, $R_2$, $R_3$, $R_4$ or $R_5$ are a methyl, ethyl, n-propyl, isopropyl, n-butyl, tert-butyl, cyclohexyl, benzyl, phenyl, 2-methyl-2-phenylprop-1-y1 residue.

Preferred non-limiting examples of aryloxy radicals are: 4-phenylphenoxy, 2-phenylphenoxy, 2,6-diphenylphenoxy, 2,4,6-triphenylphenoxy, 2,3,5,6-tetraphenylphenoxy, 2,4-ditert-butyl-6-phenylphenoxy, 2,6-diisopropylphenoxy, 2,6-dimethylphenoxy, 2,6-ditert-butylphenoxy, 4-methyl-2,6-ditert-butylphenoxy, 2,6-dichloro-4-tert-butylphenoxy, and 2,6-dibromo-4-tert-butylphenoxy. When the aryloxy hydrocarbyl aluminum compound is selected from aluminum aryloxides with general formula $RAl(R'O)_2$, the two aryloxy radicals can be carried by the same molecule such as a biphenoxy, binaphthoxy or 1,8-naphthalene-dioxy radical, which may or may not be substituted by alkyl, aryl, or halide radicals.

Particularly preferred compounds are bis(2,6-diphenylphenoxy) isobutyl aluminum or bis(2,6-diphenylphenoxy) ethyl aluminum.

The preparation of the compound $R_nAl(R'O)_{3-n}$ is known in the literature. Any process for preparing this compound may be suitable such as, for example, the reaction of a phenol R'OH with a trialkylaluminum $AlR_3$ in an organic solvent, for example a hydrocarbon or an ether.

The hydrocarbyl aluminum compounds used in the invention are represented by the general formula $AlR''_mX_{3-m}$ where R″ is a hydrocarbyl radical, preferably an alkyl radical containing 1 to 6 carbon atoms, X is a chlorine or bromine atom, preferably a chlorine atom, and m is a number in the range 1 to 3. Non limiting examples are: dichloroethylaluminum, ethylaluminum sesquichloride, chlorodiethylaluminum, chlorodiisobutylaluminum, triethylaluminum, tripropylaluminum, and triisobutylaluminum. The preferred hydrocarbyl aluminum compound is triethylaluminum.

The catalyst components can be brought into contact in a solvent constituted by a saturated hydrocarbon such as hexane, cyclohexane, heptane, butane, or isobutane, by an unsaturated hydrocarbon such as a monoolefin or a diolefin containing, for example, 4 to 20 carbon atoms, or by an aromatic hydrocarbon such as benzene, toluene, xylene, mesitylene, or ethylbenzene, used pure or as a mixture.

The concentration of chromium in the catalytic solution can vary from $1 \times 10^{-5}$ to 0.1 mole/l, preferably $5 \times 10^{-5}$ to $1 \times 10^{-2}$ mole/l. The molar ratio between the aryloxy aluminum compound and the chromium compound can be between 1:1 and 30:1, preferably between 1:1 and 20:1. The molar ratio between the hydrocarbyl aluminum and the chromium compound is selected so as to be between 1:1 and 35:1, preferably between 1:1 and 15:1.

The order of mixing the three constituents of the catalytic composition is not critical. However, the chromium compound is preferably first mixed with the aryloxy aluminum compound, and then added to the hydrocarbyl aluminum compound.

The ethylene oligomerization reaction can be carried out at a total pressure in the range 0.5 MPa and 15 MPa, preferably in the range 1 to 8 MPa, and at a temperature in the range 20° C. and 180° C., preferably in the range 50° C. to 160° C.

In one particular implementation of the catalytic oligomerization reaction carried out batchwise, a set volume of the catalytic solution, prepared as described above, is introduced into a reactor provided with the usual stirring, heating and cooling means, then pressurised with ethylene to the desired pressure, and the temperature is adjusted to the desired value. The oligomerisation reactor is kept under constant pressure by introducing ethylene until the total volume of liquid product represents, for example, between 2 and 50 times the volume of the catalytic solution initially introduced. The catalyst is then destroyed using any normal means known to the skilled person, then the reaction products and the solvent are extracted and separated.

For a continuous operation, implementation is preferably as follows: the catalytic solution is injected at the same time as the ethylene into a reactor which is stirred using conventional stirring means or by external recirculation, and kept at the desired temperature. The components of the catalyst can also be separately injected into the reaction medium, for example the product of the interaction of the chromium compound with the aryloxy aluminum compound with formula $R_nAl(R'O)_{3-n}$ and the hydrocarbyl aluminum compound represented by general formula $AlR''_mX_{3-m}$. Ethylene is introduced using a pressure activated inlet valve which keeps the pressure constant. The reaction mixture is extracted by means of a liquid level activated valve so as to maintain the liquid level constant. The catalyst is continuously destroyed using any normal means which is known to the skilled person, then the reaction products and solvent are separated, for example by distillation. Non transformed ethylene can be recycled to the reactor.

The following examples illustrate the invention without limiting its scope.

EXAMPLE 1

$0.5 \times 10^{-3}$ moles of chromium (III) 2-ethylhexanoate in solution in a mineral oil was introduced kept from humidity, into a 100 ml glass flask under an inert atmosphere and the solution was heated for one hour under a vacuum of $10^{-2}$ torr then diluted with 25 ml of toluene which had been distilled under an inert atmosphere.

The following were introduced in order under ethylene at ambient temperature into a stainless steel autoclave with a working volume of 100 ml provided with a double envelope to regulate the temperature by oil circulation: 5 ml of the chromium (III) 2-ethylhexanoate solution prepared above, i.e., $0.1 \times 10^{-3}$ moles of chromium, 8 ml of a 0.1 M bis(2,6-diphenylphenoxy)-isobutylaluminum solution in toluene, i.e., $0.8 \times 10^{-3}$ moles, and $0.8 \times 10^{-3}$ moles of triethylaluminum in solution in 8 ml of toluene. The temperature was raised to 120° C. and the ethylene pressure was kept at 5 MPa.

After one hour of reaction, introduction of ethylene was halted and the catalyst was deactivated by injecting 0.5 ml of ethanol in solution in 1.5 ml of toluene using an air lock which could be pressurised to a pressure higher than that of the autoclave. The reactor was cooled and degassed then the gas and liquid were analysed by gas chromatography. 19 g of ethylene had been consumed in one hour. The composition of the products is given in Table 1. 18% by weight of solid polymer with respect to the ethylene consumed was also recovered.

EXAMPLE 2

With the same apparatus as that used in Example 1 and under the same conditions, with the exception that half the amount of bis(2,6-diphenylphenoxy)isobutylaluminum was introduced, 12 g of ethylene was consumed in one hour of reaction. The product composition is shown in Table 1. 30% by weight of solid polymer with respect to the ethylene consumed was also recovered.

EXAMPLE 3

With the same apparatus as that used in Example 1 and under the same conditions, with the exception that no bis(2,6-diphenylphenoxy)isobutylaluminum was introduced, 1 g of ethylene was consumed in one hour of reaction. The product composition is shown in Table 1. 72% by weight of polymer with respect to the ethylene consumed was also recovered.

EXAMPLE 4

With the same apparatus as that used in Example 1 and under the same conditions, with the exception that the pressure was 3 MPa and the molar ratio of bis(2,6-diphenylphenoxy)isobutylaluminum/Cr was 5/1, 14 g of ethylene was consumed in one hour of reaction. The product composition is shown in Table 1. 20% by weight of solid polymer with respect to the ethylene consumed was also recovered.

EXAMPLE 5

With the same apparatus as that used in Example 1 and under the same conditions, with the exception that the bis(2,6-diphenylphenoxy)isobutylaluminum was replaced by bis(2,6-tert-butylphenoxy)isobutylaluminum, 5 g of ethylene was consumed in one hour of reaction. The product composition is shown in Table 1. 35% by weight of solid polymer with respect to the ethylene consumed was also recovered.

EXAMPLE 6

With the same apparatus as that used in Example 1 and under the same conditions, with the exception that the pressure was 3 MPa and the molar ratio of bis(2,6-diphenylphenoxy)isobutylaluminum/Cr was 10/1, and the triethylaluminum/Cr molar ratio was 5/1, 5 g of ethylene was consumed in one hour of reaction. The product composition is shown in Table 1. 40% by weight of solid polymer with respect to the ethylene consumed was also recovered.

EXAMPLE 7

With the same apparatus as that used in Example 1 and under the same conditions, with the exception that the bis(2,6-diphenylphenoxy)isobutylaluminum was replaced by bis-2,6-diphenylphenoxydiethylaluminum, the bis-2,6-diphenylphenoxydiethylaluminum/Cr molar ratio was 4/1 and the triethylaluminum/Cr molar ratio was 10/1, 5.4 g of ethylene was consumed in one hour of reaction. The product composition is shown in Table 1. 41% by weight of solid polymer with respect to the ethylene consumed was also recovered.

TABLE 1

| Example | Distribution of products obtained (weight %) | | | | Amount of alpha olefins (weight %) | | |
|---|---|---|---|---|---|---|---|
| | $C_4$ | $C_6$ | $C_8$ | $C_{10}^+$ | in $C_4$ | in $C_6$ | in $C_8$ |
| 1 | 0.4 | 74.5 | 0.9 | 6.2 | 87.2 | 99.8 | 96.5 |
| 2 | 5.5 | 60.6 | 1.2 | 2.7 | 92.7 | 99.6 | 95.7 |
| 3 | 19.1 | 6.5 | 0.4 | 2 | 79.3 | 55.3 | |
| 4 | 0.4 | 67.5 | 0.7 | 11.4 | 98.1 | 99.7 | |
| 5 | 18.5 | 42.6 | 1 | 2.9 | 94.4 | 95.9 | 75.3 |
| 6 | 22 | 38 | 0 | 0 | 99.4 | 99.2 | |
| 7 | 49.5 | 8.5 | 0.6 | 0.7 | 98.0 | 96.9 | |

Depending on the catalytic composition selected, the process of the invention thus essentially produces 1-butene and/or 1-hexene or mixtures thereof, to the exclusion of higher olefins, and with high selectivity for alpha olefins.

We claim:

1. A catalytic composition obtained by mixing:
   at least one chromium compound;
   with at least one aryloxy aluminum compound with general formula $R_nAl(R'O)_{3-n}$ in which n is a whole number which can take the values 0, 1 or 2, R is a linear or branched hydrocarbyl radical containing 1 to 30 carbon atoms, and R'O is an aryloxy radical containing 6 to 80 carbon atoms;
   and with at least one hydrocarbyl aluminum compound with general formula $AlR''_mX_{3-m}$ where R'' is a hydrocarbyl radical containing 1 to 6 carbon atoms, X is a chlorine or bromine atom and m is a number from 1 to 3, said at least one chromium compound and said at least one aryloxy aluminum compound and said at least one hydrocarbyl aluminum compound being present in such proportions as to provide catalytic activity to the catalytic composition.

2. A composition according to claim 1, wherein the chromium compound comprises one or more identical or different anions selected from the group consisting of halides, carboxylates, acetylacetonates, and alkoxy and aryloxy anions.

3. A composition according to claim 1, wherein in the aryloxy aluminum compound with general formula $R_nAl(R'O)_{3-n}$, the aryloxy radical R'O has general formula:

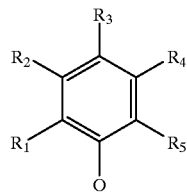

where $R_1$, $R_2$, $R_3$, $R_4$, $R_5$, which may be identical or different, represent a hydrogen, a halogen or a hydrocarbyl radical containing 1 to 16 carbon atoms.

4. A composition according to claims 1, wherein the aryloxy aluminum compound is bis(2,6-diphenylphenoxy) isobutylaluminium or bis(2,6-diphenylphenoxy) ethylaluminum.

5. A composition according to claim 1, wherein the hydrocarbyl aluminum compound is dichloroethylaluminum, ethylaluminum sesquichloride, chlorodiethylaluminum, chlorodiisobutylaluminum, triethylaluminum, tripropylaluminum, or triisobutylaluminum.

6. A composition according to claim 1, wherein the hydrocarbyl aluminum compound is triethylaluminium.

7. A composition according to claim 1, wherein the catalyst components are brought into contact in a at least one saturated, unsaturated, olefinic, diolefinic or aromatic hydrocarbon solvent.

8. A composition according to claim 7, wherein the concentration of chromium in the catalytic solution is in the range $1 \times 10^{-5}$ to 0.1 mole/l.

9. A composition according to claim 1, wherein the molar ratio between the aryloxy aluminum compound and the chromium compound is in the range 1:1 to 30:1 and the mole ratio between the hydrocarbyl aluminum and the chromium compound is in the range 1:1 to 35:1.

10. An ethylene oligomerisation process comprising oligomerising ethylene in contact with a catalytic quantity of a catalytic composition according to claim 1 under oligomerizing conditions.

11. A process according to claim 10, wherein the ethylene oligomerisation reaction is carried out at a pressure in the range 0.5 MPa to 15 MPa and at a temperature in the range 20° C. to 180° C.

12. A composition according to claim 2, wherein in the aryloxy aluminum compound with general formula $R_nAl(R'O)_{3-n}$, the aryloxy radical R'O has general formula:

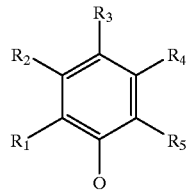

where $R_1$, $R_2$, $R_3$, $R_4$, $R_5$, which may be identical or different, represent a hydrogen, a halogen or a hydrocarbyl radical containing 1 to 16 carbon atoms.

13. A composition according to claim 2, wherein the aryloxy aluminum compound is bis(2,6-diphenylphenoxy) isobutylaluminium or bis(2,6-diphenylphenoxy) ethylaluminium.

14. A composition according to claim 3, wherein the hydrocarbyl aluminum compound is dichloroethylaluminum, ethylaluminum sesquichloride, chlorodiethylaluminum, chlorodiisobutylaluminum, triethylaluminum, tripropylaluminum, or triisobutylaluminum.

15. A composition according to claim 13, wherein the hydrocarbyl aluminum compound is triethylaluminium.

16. A composition according to claim 14, wherein the molar ratio between the aryloxy aluminum compound and the chromium compound is in the range 1:1 to 30:1 and the mole ratio between the hydrocarbyl aluminum and the chromium compound is in the range 1:1 to 35:1.

17. A composition according to claim 15, wherein the molar ratio between the aryloxy aluminum compound and the chromium compound is in the range 1:1 to 30:1 and the mole ratio between the hydrocarbyl aluminium and the chromium compound is in the range 1:1 to 35:1.

18. An ethylene oligomerization process comprising oligomerising ethylene in contact with a catalytic quantity of a catalytic composition according to claim 5 under oligomerizing conditions.

19. An ethylene oligomerization process comprising oligomerising ethylene in contact with a catalytic quantity of a catalytic composition according to claim 16 under oligomerizing conditions.

20. An ethylene oligomerization process comprising oligomerising ethylene in contact with a catalytic quantity of a catalytic composition according to claim 17 under oligomerizing conditions.

21. An ethylene oligomerization process comprising oligomerising ethylene in contact with a catalytic quantity of a catalytic composition according to claim 9 under oligomerizing conditions.

22. A composition according to claim 9, wherein the molar ratio between the aryloxy aluminum compound and the chromium compound is in the range of 1:1 to 20:1 and the molar ratio of the hydrocarbyl aluminum to the chromium compound is in the range of 1:1 to 15:1.

23. A composition according to claim 16, wherein the molar ratio between the aryloxy aluminum compound and the chromium compound is in the range of 1:1 to 20:1 and the molar ratio of the hydrocarbyl aluminum to the chromium compound is in the range of 1:1 to 15:1.

24. A composition according to claim 17, wherein the molar ratio between the aryloxy aluminum compound and the chromium compound is in the range of 1:1 to 20:1 and the molar ratio of the hydrocarbyl aluminum to the chromium compound is in the range of 1:1 to 15:1.

25. An ethylene oligomerization process comprising oligomerising ethylene in contact with a catalytic quantity of a catalytic composition according to claim 22 under oligomerizing conditions.

26. An ethylene oligomerization process comprising oligomerising ethylene in contact with a catalytic quantity of a catalytic composition according to claim 23 under oligomerizing conditions.

27. An ethylene oligomerization process comprising oligomerising ethylene in contact with a catalytic quantity of a catalytic composition according to claim 24 under oligomerizing conditions.

* * * * *